United States Patent [19]
Dinelli et al.

[11] 3,947,325
[45] Mar. 30, 1976

[54] PREPARATION OF HIGH PERMEABILITY CELLULOSE FIBERS CONTAINING ENZYMES

[75] Inventors: Dino Dinelli, San Donato Milanese; Francesco Bartoli, Rome; Silvio Gulinelli, Monterotondo, all of Italy

[73] Assignee: Snamprogetti S.p.A., San Donato Milanese, Italy

[22] Filed: Apr. 11, 1974

[21] Appl. No.: 460,225

[52] U.S. Cl. .............. 195/68; 195/63; 195/DIG. 11
[51] Int. Cl.² ........................................... C07G 7/02
[58] Field of Search ............... 195/63, 68, DIG. 11; 264/49

[56] References Cited
UNITED STATES PATENTS
3,715,277   2/1973   Dinelli et al. .......................... 195/63
FOREIGN PATENTS OR APPLICATIONS
953,414   3/1964   United Kingdom

OTHER PUBLICATIONS

Thang et al., Observations on the Activity of Enzymes After Filtration On (and Through) a Nitrocellulose Membrane, Biochemical and Biophysical Research Communications, Vol. 31, No. 1, 1968 (pp. 1–8).

*Primary Examiner*—David M. Naff
*Attorney, Agent, or Firm*—Ralph M. Watson

[57]                ABSTRACT

High permeability cellulose fibers containing enzymes are formed by preparing a solution of nitrocellulose in a solvent that is insoluble in water, preparing an aqueous enzyme solution, mixing together the nitrocellulose and enzyme solutions and emulsifying the mixture, spinning the emulsion into a coagulating bath to produce fibers englobing enzymes and treating the fibers with a reducing agent under conditions which do not damage the enzymes so that nitro groups are removed from the nitrocellulose.

5 Claims, No Drawings

PREPARATION OF HIGH PERMEABILITY CELLULOSE FIBERS CONTAINING ENZYMES

The present invention relates to the preparation of high permeability cellulose fibers having enzymes englobed therein.

It is known that many reactions, which otherwise might not be performed or would need more drastic operating conditions, can be readily carried out when catalyzed by enzymes.

It is also known that use may be made of fibers englobing enzymes which carry out their catalytic activity without spreading into the reaction mass. The inclusion of the enzyme is carried out by employing a fiber constituted by an artificial or synthetic polymeric material.

The fibers englobing enzymes can be prepared by starting with polymer solutions adapted to give fibers wherein enzymatic compounds are dispersed in the form of very small drops of the order of magnitude of emulsions.

The so obtained emulsion may be wet or dry spun to produce a fiber presenting, in its interior, very small cavities which contain the enzymes so that they are separated from the environment by a very thin membrane.

The fibers englobing enzymes, employed to date employed and constituting the subject of Italian patent no. 836,462 (and the corresponding U.S. Pat. No. 3,715,277) in the name of the assignee of this application are obtained by starting with polymers adapted to give fibers such as, for instance, cellulose derivatives, but nothing is known about the fact that they can be prepared by starting with just the unregenerated cellulose because of the difficulties this latter presents when subjected to the ensuing spinning processes.

The use of cellulose fibers englobing the enzymes has the advantage, with respect to the other kinds of fibers, of a higher activity with respect to enzymatic reactions, because of the increased permeability of the fiber itself. In fact the catalytic action of the enzymes contained in fibers is affected by its availability, therefore the enzymatic activity depends on the permeability of the fibers.

It is not always possible to obtain high premeability fibers englobing enzyme by simply affecting the fiber preparation conditions, owing to the fact that, at high enzyme concentrations, the permeability is still a limiting factor.

We have found, and this is an aspect of the present invention, that it is possible to prepare cellulose fibers englobing enzymes by starting with a substituent-containing cellulose polymer which is suitably emulsified with an enzymatic solution, then spun and, finally, the so obtained fibers are subjected to reactions through which the substituents are removed: an unsubstituted cellulose base fiber englobing the enzyme is so obtained, which has a permeability very much higher than that of the substituted cellulose base fiber. The process according to the present invention is fundamentally based on a chemical modification of the starting fibrous material through the action of reducing agents under operating conditions that do not damage the enzyme.

The inventive process makes it possible to overcome the above cited drawbacks and the fibers englobing enzymes, obtained after the reduction process and constituting a second aspect of the invention, have a high degree of permeability.

The employed starting material fundamentally consists of high molecular weight nitrocellulose with such a nitrogen content (preferably higher than 5%) that it renders the material substantially soluble in organic solvents.

It is dissolved in a solvent, immiscible with water, selected from n-butyl-acetate, bis-butylphtalate, methylamylketone, ethylamylketone and others which can be employed as such or suitably diluted by aliphatic hydrocarbons such as pentane, hexane, heptane, octane, aromatic hydrocarbons such as toluene and xylene, or hydrocarbon mixtures such as ligroin.

To the cellulose solution is added the aqueous solution containing the enzymes which may be selected from a wide class. For instance use may be made urease, invertase, lactase, acylase, transaminase, glucose-oxidase, catalase, papain, penicillin acylase and others. The emulsion is then spun according to known techniques by using known coagulants such as, for instance, the ones cited in the abovementioned Italian and U.S. Pats. Besides the process of emulsion dispersion of the enzyme into the polymer solution, other processes can be performed in order to prepare fibers englobing the enzyme. For instance said enzyme can be dispersed, as a powder, into the polymer which will then be spun according to known methods. The so obtained fiber is reacted with a reducing agent which removes nitro groups and forms the cellulose fiber englobing the enzyme, which is the subject of the present invention.

A solution of ammonium sulfhydrate with or without excesses of ammonia or hydrogen sulphide may be used as reducing agent.

Further operating details will be clear from examining the examples hereinafter reported.

EXAMPLE 1

1,000 g. of nitrocellulose (of Snia Viscosa S.p.A) were dissolved into a solution constituted by 6,900 g. of n-butylacetate and 4,600 g. of toluene. Then there were added 1,600 g. of an aqueous solution containing the enzyme invertase.

Under stirring, an emulsion was obtained which was spun through orifices having a 125 $\mu$ diameter by using a coagulating agent constituted by a mixture of saturated hydrocarbons having boiling points ranging from 40° to 70°C. About 2,600 g. of fiber englobing the enzyme were obtained.

1,000 g. of this fiber, immersed in a 20% saccharose solution at a pH of 4.5 inverted 40 g. of sugar per minute. 1,000 g. of fiber were treated with a 2% ammonia solution, which had been saturated with hydrogen sulphide up to a pH of 8.5.

After 6 reaction hours, this second fiber was washed and, when immersed in a 20% saccharose solution at a pH of 4.5, it inverted 490 g of sugar per minute.

EXAMPLE 2

1,000 g. of nitrocellulose (of Snia Viscosa S.p.A.) were dissolved, at room temperature, in a mixture constituted by 7,000 g. of n-butylacetate and 3,750 g. of toluene. 2,000 g. of an aqueous solution of the enzyme invertase were added to the obtained solution.

An emulsion was obtained under stirring: at 1°C it was spun through orifices having a 125 $\mu$ diameter and coagulated, at 20°C, in a mixture of saturated hydrocarbons having boiling points ranging from 60° to 80°C. About 3,000 g. of fiber were obtained.

1,000 g. of this fiber, immersed in a 20% saccharose solution at a pH of 4.5 inverted 505 g. of sugar per minute.

Another 1,000 g. of fiber were treated, over 6 hours, with an ammonia solution saturated with hydrogen sulphide according to example 1. After the treatment, the resulting fiber, immersed in a saccharose solution like the one of the preceding example, inverted 1890 g. of sugar per minute.

EXAMPLE 3

1,000 g. of nitrocellulose (of Snia Viscosa S.p.A.) were dissolved into a mixture constituted by 7,000 g. of n-butylacetate and 3,750 g. of toluene.

Then 2,000 g. of an aqueous solution of the enzyme penicillin acylase were added and the whole was stirred up to an emulsion.

The emulsion was spun according to example 1 and 3,000 g. of fiber were obtained. 1,500 g. of fiber were immersed in 37.5 liters of a $10^{-1}$ M potassium phosphate solution at pH of 8.0 containing 1,500 g. of potassium penicillin G, at 37°C. The enzyme contained in the fiber catalyzed the hydrolysis of penicillin to 6-amminopenicillanic acid and phenyl-acetic acid.

During the reaction the pH was kept constant by adding sodium hydroxide. In such a way a 90% conversion of penicillin was obtained after 227 minutes.

2,000 g. of an aqueous solution of the enzyme penicillin-acylase were englobed in 1,000 g. of nitrocellulose according to the procedure described above and then treated with the ammonia solution saturated with hydrogen sulphide as described in example 1.

A like solution of penicillin-acylase was dispersed in a solution formed by dissolving 1,000 g. of cellulose triacetate in 13,300 g. of methylene chloride. This emulsion was spun as described in example 1, the coagulant being toluene. 1,000 g. of the first fiber, at 37°C immersed in 25 liters of a $10^{-1}$ M potassium phosphate solution at pH of 8.0 containing potassium penicillin G at 10%., hydrolized 90% of penicillin over 219 minutes.

The second fiber, under the same conditions, hydrolized 90% of penicillin over 298 minutes.

Another 1,500 g. of fiber were treated with the ammonia solution saturated with hydrogen sulphide as described in example 1. Then, under the same conditions as the untreated fiber, they promoted the conversion of 90% of penicillin over 56 minutes.

It is obvious that what has been said with respect to fibers might be extended to films, microcapsules or similar products containing enzymes.

The special interest of the assignee of this application in the fiber field has prompted us to describe only enzyme englobing fibers in the specific examples; but it will be appreciated that our invention may be practiced through the use of other enzyme containing products without departing from the spirit thereof.

What we claim is:

1. The process of preparing cellulose fibers of high permeability containing englobed enzymatic material adapted to exert catalytic activity in enzymatic reactions, which consists of the steps of dissolving nitrocellulose in a solvent which is insoluble in water, preparing an aqueous solution of said enzymatic material, emulsifying said solutions, spinning said emulsion into a coagulating bath to produce nitrocellulose fibers containing englobed enzymatic material, and then treating said fibers with a reducing agent under operating conditions which do not damage the enzymatic material so that nitro groups are removed from said nitrocellulose.

2. A process as claimed in claim 1, wherein the reducing agent is an ammonium sulfhydrate solution or a mixture thereof with a slight excess of ammonia or hydrogen sulphide.

3. A process as claimed in claim 1, wherein said solvent insoluble in water is a member of the group consisting of n-butylacetate, bis-butylphtalate, methylamylketone and ethylamylketone.

4. A process as claimed in claim 1, wherein said solvent insoluble in water contains a diluent selected from the group consisting of aliphatic hydrocarbons, aromatic hydrocarbons and mixtures of hydrocarbons.

5. A process as claimed in claim 1, wherein the englobed enzymatic material is a member of the group consisting of urease, invertase, lactase, acylase, transaminase, glucose-oxidase, catalase, papain, tryptophan synthetase and penicillin acylase.

* * * * *